(12) United States Patent
Donovan et al.

(10) Patent No.: US 8,568,714 B2
(45) Date of Patent: Oct. 29, 2013

(54) LYS K ENDOLYSIN IS SYNERGISTIC WITH LYSOSTAPHIN AGAINST MRSA

(75) Inventors: David M. Donovan, Baltimore, MD (US); Stephen C. Becker, Baltimore, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 285 days.

(21) Appl. No.: 12/470,466

(22) Filed: May 21, 2009

(65) Prior Publication Data

US 2010/0021450 A1    Jan. 28, 2010

Related U.S. Application Data

(60) Provisional application No. 61/128,707, filed on May 23, 2008.

(51) Int. Cl.
*A61K 38/46*    (2006.01)

(52) U.S. Cl.
USPC ....................................................... 424/94.6

(58) Field of Classification Search
None
See application file for complete search history.

(56) References Cited

U.S. PATENT DOCUMENTS

2003/0211995 A1*  11/2003  Kokai-Kun et al. ............ 514/12

OTHER PUBLICATIONS

O'Flaherty et al. (J. Bacteriol., 187:7161-7164, 200.*
Donovan et al. (FEMS Microbiol. Lett., 265:133-139, 2006).*

* cited by examiner

*Primary Examiner* — Brian J Gangle
(74) *Attorney, Agent, or Firm* — John D. Fado; Evelyn M. Rabin (57) ABSTRACT

Multi-drug resistant superbugs are a persistent problem in modern health care. LysK is a staphylococcal bacteriophage endolysin from the phage K. It is a peptidoglycan hydrolase enzyme that can lyse many staphylococcal strains and thus is a potent antimicrobial against *S. aureus*, including MRSA. Lysostaphin is a bacteriocin secreted by *S. simulans* to kill *S. aureus*, and has been shown to also be a potent antimicrobial for many antibiotic resistant strains of *S. aureus*. This study describes optimal reaction conditions for the recombinant His-tagged LysK protein, compares its MIC and antimicrobial activity to lysostaphin and demonstrates synergy when the two are used in combination against the MRSA USA300.

8 Claims, 6 Drawing Sheets

LYS K ENDOLYSIN IS SYNERGISTIC WITH LYSOSTAPHIN AGAINST MRSA

This application claims the benefit of U.S. Provisional Application No. 61/128,707, filed May 23, 2008, which is incorporated herein by reference in its entirety.

BACKGROUND OF THE INVENTION

1. Field of the Invention

This invention relates to a pathogen-specific composition comprising a peptidoglycan hydrolase, LysK endolysin, and another peptidoglycan hydrolase, lysostaphin. The LysK endolysin specifically attacks the peptidoglycan cell wall of untreated, live staphylococci including *S. aureus* and methicillin-resistant *Staphylococcus aureus* (MRSA); lysostaphin is a potent anti-staphylococcal bacteriocin. The LysK endolysin—lysostaphin dual enzyme composition acts synergistically and lyses untreated, live MRSA with enhanced efficacy at dosages that are ineffective when used alone. The invention further relates to methods of treating *Staphylococcus*-induced diseases such as mastitis and staphylococcal infections, such as MRSA-induced infections.

2. Description of the Relevant Art

Antimicrobial resistance is such a nationwide concern that many agencies within the Department of Health and Human Services (DHHS), e.g. FDA, USDA, NIH, and CDC have formed a taskforce to address the issue Retrieved from the Internet: <URL: cdc.gov/drugresistance/actionplan/2005report/index.htm. Multi-drug resistance pathogens are no longer just nosocomiaf, but are now often community acquired (File, Jr. 2007. *Cleve. Clin. J. Med.* 74(Suppl. 4): S6-11, 86-11; Furuya et al. 2007. *Am. J. Infect. Control* 35:359-366). Methicillin resistant *Staphylococcus aureus* (MRSA) is one of the most notorious drug resistant pathogens; the press has been filled with recent articles about the threat of these new "superbugs" for which new antimicrobials are sorely needed. The DHHS antimicrobial taskforce recommendations include research and development of novel antimicrobials that avoid resistance development.

Bacteriophage endolysins are peptidoglycan hydrolases that normally help the newly replicated phage particles escape from the host bacteria at the end of the phage lytic cycle. Each lytic phage genome encodes proteins that degrade the bacterial cell wall peptidoglycan and allow the newly replicated phage to escape. In addition to causing cell lysis when released from within the host, they are also evolving as a new class of candidate antimicrobial able to lyse Gram positive cells when exposed externally "from without." They are uniquely specific to the cell wall peptidoglycan of their host (or closely related species), thus reducing the risk of resistance development in non-pathogenic commensal bacteria associated with broad range antibiotic use. In addition, presumably due to the co-evolution of phage and host of the few phage lysins that have been examined, all are refractory to resistance development, making them ideally suited to address the current problem of multi-drug resistant pathogens (reviewed in Fischetti, V. A. 2005. *Trends Microbiol.* 13: 491-496).

Many phage endolysins show promise in pre-clinical trials when used to cure animal models of human disease. A streptococcal bacteriophage lytic enzyme was successful in the treatment of streptococci from rats in an experimental endocarditis (Entenza et al. 2005. *Antimicrobial Agents and Chemotherapy* 49: 4789-4792). Similarly, phage lytic enzymes achieved mucosal clearing in streptococcal infection models when applied to the murine vagina, oropharynx (Cheng et al. 2005. *Antimicrob. Agents Chemother.* 49: 111-117; Fischetti, V. A. 2003. *Ann. N. Y. Acad. Sci.* 987: 207-214; Loeffler et al. 2003. *Infection and Immunity* 71:6199-6204), and oral cavity (Nelson et al., 2001. *Proc. Nat. Acad. Sci. U.S.A.* 98 (7): 4107-4112). Murine models of anthrax were also cured with endolysins (Schuch et al. 2002. *Nature* 418: 884-889). In vitro studies indicate serum antibodies to phage endolysins slowed but did not block in vitro killing of the target microbes *Bacillus anthracis, Streptococcus pyogenes*, or *Streptococcus pneumoniae* (Fischetti 2005, supra; Jado et al. 2003. *J. Antimicrob. Chemother.* 52 (6): 967-973; Loeffler et al., supra).

One recently described phage endolysin, LysK, can kill a wide range of staphylococci including multiple MRSA in plate lysis assays (O'flaherty et al. 2005. *J. Bacteriol.* 187: 7161-7164). This endolysin from the phage K is virtually identical to the phage 812 (ABL87139) and phage G1 (electronically spliced ORF 42 and 60 of genome AY954969) endolysins. Interestingly, each contains an intron in their endolysin gene, an unusual feature among phage genomes. Blast analysis of the LysK protein sequence reveals two lytic domains, a Cysteine, Histidine-dependent Amidohydrolase/Peptidase (CHAP) endopeptidase domain, an amidase (N-acetyl-muramyl-L-alanine amidase) domain, and a C-terminal SH3b cell wall binding domain (O'Flaherty et al., supra). It is common for phage endolysins to have an N-terminal lytic domain (or two) with a C-terminal cell wall binding domain (Loessner, M. J. 2005. *Curr. Opin. Microbiol.* 8 (4): 480-487), although recently an endolysin with two lytic domains flanking two mid-protein cell wall binding domains (Cpl-1) was reported for the LambdaSa2 prophage (Pritchard et a. 2007. *Appl. Environ. Microbiol.* 73: 7150-7154).

Another potent peptidoglycan hydrolase antimicrobial is lysostaphin which cleaves the pentaglycine interpeptide bridge of *S. aureus* cell walls. Lysostaphin was discovered more than 50 years ago (Browder et al. 1965. *Biochem. BioPhys. Res. Comm.* 19: 383-389), and is a potent anti-staphylococcal bacteriocin synthesized by *S. simulans* that kills *S. aureus* through digestion of the peptidoglycan with high species-specificity. This specificity was first shown to require the C-terminal 92 amino acids, with this protein fragment able to direct binding of heterologous proteins to the *S. aureus* cell wall (Baba and Schneewind. 1996. *EMBO Journal* 15: 4789-4797). The exact site of binding was demonstrated by two laboratories to be the pentaglycine interpeptide bridge which is cleaved (Grundling and Schneewind. 2006. *J. Bacteriol.* 188: 2463-2472; Lu et al. 2006. *J. Biol. Chem.* 281:549-558). Lysostaphin kills MRSA (Dajcs et al. 2000. *Am. J. Ophthalmol.* 130: 544), planktonic *S. aureus* (Walencka et al. 2005. *Pol. J. Microbiol.* 54:191-200; Wu et al. 2003. *Antimicrobial Agents and Chemotherapy* 47: 3407-3414), vancomycin-intermediate *S. aureus* (Patron et al. 1999. *Antimicrobial Agents and Chemotherapy* 43:1754-1755), and other antibiotic-resistant strains of *S. aureus* (Bhakta et al. 2003. *Indian J. Med. Res.* 117:146-151). It is also active against *S. aureus* biofilms (Walencka et al., supra; Wu et al., supra), and exhibits limited activity against many coagulase negative staphylococci (Cisani et al. 1982. *Antimicrobial Agents and Chemotherapy* 21:531-535; McCormick et al. 2006b. *Curr. Eye Res.* 31:225-230; Zygmunt et al. 1968. *Appl. Microbiol.* 16:1168-1173).

Lysostaphin has a long history of successfully treating livestock and animal models of human disease. Treatment of mouse models with lysostaphin was initiated as early as the 1960s (reviewed in Climo et al. 1998. *Antimicrobial Agents and Chemotherapy* 42:1355-1360). In treating *S. aureus* bovine mastitis, intramammary infusions did not raise a significant immune response until 18 to 21 injections, while seven once-daily injections were curative (Oldham and Daley. 1991. *J. Dairy Sci.* 74: 4175-4182). In a *S. aureus* endocarditis model, systemic lysostaphin treatment yielded minimal adverse effects (Climo et al., supra). Lysostaphin (15 mg/kg) given by i.v. for 9 weeks resulted in serum antibodies to lysostaphin and an eight-fold reduction in its lytic activity, but no adverse immune response (Schaffner et al. 1967. *Yale J. Biol. Med.* 39: 230-244). More recent studies demonstrate the efficacy of lysostaphins for curing rat nasal colonization (Kokai-Kun et al. 2003. *Antimicrobial Agents and Chemotherapy* 47: 1589-1597) and rat neonatal *S. aureus* infections (Oluola et al. 2007. *Antimicrobial Agents and Chemotherapy* 51:2198-2200). Lysostaphin has also been shown to be effective in a rabbit model of endophthalmitis against coagulase negative staphylococci (McCormick et al. 2006a. *Curr. Eye Res.* 31:225-230). Lysostaphin expression as a transgenic antimicrobial protects mice and cattle from an intra-mammary challenge by *S. aureus* (Kerr et al. 2001. *Nat. Biotech.* 19: 66-70; Wall et a. 2005. *Nat. Biotechnol.* 23: 445-451). There has been a flood of recent patent applications that take advantage of lysostaphin and phage proteins as antimicrobials (Donovan, D. M. 2007. *Recent Patents in Biotechnology* 1:113-122).

The use of peptidoglycan hydrolase enzymes as antimicrobials has been tested in combinations with other antimicrobials. Lysostaphin has been shown to be synergistic with β-lactams against oxacillin-resistant *S. epidermidis* (Kiri et al. 2002. *Antimicrobial Agents and Chemotherapy* 46:2017-2020), with the catanionic peptide ranalexin against MRSA (Graham and Coote. 2007. *J. Antimicrob. Chemother.* 59:759-762), and with beta-lactam antibiotics (including benzylpenicillin, methicillin, and cephalosporin B), bacitracin, or polymyxin B, against five clinical *S. aureus* isolates including MRSA (Polak et al. 1993. *Diagn. Microbiol Infect. Dis.* 17: 265-270.). Numerous other pathogens were tested for synergy with cationic antimicrobial peptides and lysostaphin. None were affected except *S. aureus*. Similarly, the phage lytic enzyme Cpl-1 was synergistic with gentamycin, penicillin and with the phage endolysin Pal against several penicillin-resistant and -sensitive *S. pneumonia* strains (Djurkovic et at 2005. *Antimicrobial Agents and Chemotherapy* 49:1225-1228.; Loeffler and Fischetti. 2003. *Antimicrobial Agents and Chemotherapy* 47: 375-377). A recent patent application (Kokai-Kun, J. F. 2003. US 20030211995) indicates there is synergy with lysostaphin and the phi11 endolysin or the antibiotic bacitracin against *S. aureus*.

To reduce the use of broad range antibiotics and thus decrease the chance of antibiotic resistance development, our goal is to develop pathogen-specific agents that are effective for the treatment of mastitis and as well as for the treatment of clinical multidrug-resistant bacteria, in particular staphylococci, that have developed resistance to antimicrobial drugs. Methicillin/oxacillin-resistant *S. aureus* is an example of such multi-drug resistant staphylococci. In this study, we examine some basic properties of the LysK enzyme in order to optimize for its antimicrobial activity and examine the use of His-tagged variants of LysK together with recombinantly produced lysostaphin to demonstrate synergy against the MRSA strain USA300.

SUMMARY OF THE INVENTION

We have discovered that a composition comprising LysK endolysin, a protein which specifically attacks the peptidoglycan cell wall of live, untreated *S. aureus* from without and lysostaphin can be used as an antimicrobial treatment for mastitis as well as for other *S. aureus* infections and for other human diseases, such as infection and disease caused by multidrug-resistant staphylococci.

In accordance with this discovery, it is an object of the invention to provide a composition comprising LysK endolysin and lysostaphin polypeptides, including recombinant LysK endolysin comprising an engineered his tag at the C-terminus.

It is also an object of the invention to provide an antimicrobial LysK endolysin—lysostaphin composition which is functional, i.e., retains its properties for degrading the peptidoglycan cell wall of untreated, live *Staphylococcus aureus* including MRSA.

An added object of the invention is to provide a composition comprising LysK endolysin and lysostaphin polypeptides according to the invention, each which allows *Staphylococcus*-induced disease and infection to be treated including those caused by MRSA.

An added object of the invention is to provide compositions useful for the treatment of diseases and infections caused by the bacteria for which the LysK endolysin and lysostaphin are specific where the composition comprises LysK endolysin and lysostaphin each in amounts that are ineffective alone but act synergistically together to effectively treat said diseases and infections.

Also part of this invention is a kit, comprising a composition for treatment of disease caused by the bacteria for which the LysK endolysin and lysostaphin are specific.

Other objects and advantages of this invention will become readily apparent from the ensuing description.

BRIEF DESCRIPTION OF THE DRAWINGS

FIG. 1A depicts a schematic of lysostaphin, and C-terminal His-tagged LysK proteins. The recombinant lysostaphin used in this work (Sigma-Aldrich Chem. Co, L0761) harbors only the 246 amino acids of the mature protein. FIG. 1B shows the SDS PAGE and zymogram analysis of 10 μg of LysK construct. Lane M, protein size markers; Lane 1. SDS Page of C-His-LysK. Lane 2. zymogram analysis of C-His-LysK. Non-tagged LysK MW=54 kD, His-tagged=55.8 kD.

FIGS. 2A, 2B and 2C depict the optimization of the turbidity reduction assay conditions for His-tagged LysK and lysostaphin. Squares=LysK, Circles=lysostaphin.

FIGS. 3A-3D depict the optimization of osmolytes used for long term storage of His-tagged LysK. LysK was stored in 400 mM NaCl, 10 mM DTT, 20 mM Tris HCl pH 7.5 supplemented with: 1% Glycerol (FIG. 3A), 25% glycerol (FIG. 3B), 2M Proline with 1% glycerol (FIG. 3C), or 1M trehalose with 1% glycerol (FIG. 3D). Open bars represent storage at −80° C., black bars represent storage at 4° C. Error bars indicate standard deviation of 3 replicates using 10 μg protein for each replicate. There is no significant difference between −80° C. treatments (p=0.062; Anova). At 4° C. the 1% glycerol maintains the highest antimicrobial activity against live cells at 30 days (p<0.001; Anova with Tukeys post hoc analysis).

DETAILED DESCRIPTION OF THE INVENTION

The increased incidence of bacterial antibiotic resistance has led to a renewed search for novel antimicrobials. *S. aureus* has a high negative impact worldwide as a multi-drug resistant pathogen for humans, e.g., MRSA and as an organism responsible for causing mastitis, an infection of dairy cattle mammary glands. Bacteriophage endolysins, as described above, are bacteriophage-encoded enzymes which degrade the peptidoglycan component of the bacterial cell wall to allow the nascently formed bacteriophage to escape. Through digestion of the peptidoglycan, endolysins can specifically lyse host bacterial cells, a characteristic that makes them an excellent source of new antimicrobial agents.

Bacterial peptidoglycan has a complex structure (sugar backbone of alternating units of N-acetyl glucosamine and N-acetyl muramic acid (NAM) residues, cross-linked by oligopeptide attachments at the NAMs. Endolysins have evolved a modular design to deal with this complexity. One protein can harbor multiple domains, each with a different peptidoglycan digestion activity. Three classes of endolysin domains have been identified thus far: endopeptidase, glycosidase, and amidase. Each has been localized to short protein domains (~100-200 amino acids). Any one of these domains is sufficient to lyse the bacterial target cell.

The Lys K endolysin was first described in 2005 when isolated from Phage K and expressed in lactococci in the laboratory of Paul Ross (O'Flaherty et al., supra). It has not been characterized for its exact peptidoglycan degrading enzymatic activities. To demonstrate LysK expression from an *E. coli* vector, the phage K endolysin gene cDNA (LysK, has an intron) was subcloned from the source vector (pQE30 from Paul Ross) into the pET21a vector, which adds six histidine codons at the C-terminus. This construct (C-His-LysK) retains all the sequences for both amidase and endopeptidase activities, according to the domain databases. With the addition of six histidines, the protein can be isolated and purified via nickel column chromatography.

Lysostaphin is a potent antimicrobial that has been tested in many different model systems (see introduction). Lysostaphin is another peptidoglycan hydrolase; it is a potent antistaphylococcal bacteriocin synthesized by *S. simulans* as a Prepro protein. The Prepro protein is proteolytically processed to the mature 246 amino acid form when secreted. The mature protein kills *S. aureus* through digestion of the peptidoglycan with high specificity. Likewise, C-His-LysK has been shown to be effective in plate lysis assays against multiple staphylococci, including MRSA strains. In order to further quantify the antimicrobial activity of C-His-LysK, we have optimized and tested its activity on live cells in the turbidity reduction assay and MIC (Minimal Inhibitory Concentration) assay. In the turbidity reduction assay, C-His-LysK was shown to have an optimal salt concentration of ~400 mM and to maintain this high activity across a broad pH range, including physiological pH 7.5. We also tested several osmolytes to determine the optimal storage conditions of the C-His-LysK. It was shown that storage at −80° C. with the addition of 1% glycerol shows the same activity as day zero against live staphylococci for 30 days or more (within standard deviation). One percent glycerol alone was a better cryoprotectant than 2M Proline+1% glycerol, 1M Trehalose+1% glycerol and 25% glycerol. In our MIC assays, lysostaphin has an MIC of 0.096 µg/ml+/−0.018, C-His-Lys K has an MIC of 32.85+4.87 µg/ml, and in combination C-His-Lys K and lysostaphin show strong synergy against the MRSA USA 300.

The MIC for lysostaphin is within the range of previously reported minimal concentrations of lysostaphin necessary to inhibit the growth of *S. aureus* (Cisani et al., supra; Graham and Coote, supra; Kusuma and Kokai-Kun, supra). The LysK MIC is within the range of MICs reported previously for the Pal and Cpl-1 endolysins of streptococcal phage origin (Loeffler and Fischetti, supra). At first glance, these MICs seem high for an antimicrobial. In fact, it would be unusual to treat an individual with an antibiotic at such high concentrations. However, it should be noted that these are enzymes and thus have very high molecular weights compared to antibiotics. For example, Ampicillin has a MW of ~400 daltons while LysK has a molecular weight of 55.8 kD. Ampicillin has an MIC of ~0.4 µg/ml on *S. aureus* strain 305 (data not shown) while we show LysK to have an MIC of ~32 µg/ml against both the MRSA USA300 and strain *S. aureus* 305. These MICs translate into ~1 micromolar ampicillin and 573 nanomolar LysK. Thus, LysK is demonstrating a very similar activity on a molar basis. The MIC for lysostaphin is comparable to or lower than the MIC for ampicillin, and thus unusually low for an agent of such high molecular weight (25.4 kD). This phenomenon cannot be readily explained.

His tags have been shown to alter protein properties (Mason et al. 2002. *Biochem.* 41: 9448-9454; McDonald et al. 2007. *Acta Crystallogr. D. Biol. Crystallogr.* 63: 891-905; Mohanty and Wiener. 2004. *Protein Expr. Purif.* 33: 311-325; Perron-Savard et al. 2005. *Microbiology* 151: 3979-3987; Tang et al. 2000. *Protein Eng.* 13: 283-289). It is known that a His-tag can effect oligomerization (Perron-Savard et al., supra), conformation of the protein (McDonald et al., supra), and in one study demonstrated a generally negative effect on solubility for multiple human proteins (Woestenenk et al. 2004. *J. Struct. Funct. Genomics* 5: 217-229). We find that the addition of 1% glycerol helps to reduce the solubility problems we faced with His-tagged LysK, and other endolysins (data not shown), but does not significantly alter the antimicrobial activity.

The ability of staphylococcal strains to develop resistance to LysK is expected to be a very rare event. In fact, no strains have been identified to date that can resist lysis by their phage endolysin (reviewed in Fischetti, supra). However, there are known mechanisms of lysostaphin resistance. The most well characterized are the lysostaphin immunity factor (lif) gene [same as endopeptidase resistance gene (epr)] (DeHart et al. 1995. *Appl. Environ. Microbiol.* 61:1475-1479) that resides on a native plasmid (pACK1) (Thumm and Gotz. 1997. *Mol. Microbiol.* 23:1251-1265), and the femA gene (factor essential for methicillin resistance) (Sugai et al. 1997. *J. Bacteriol.* 179: 4311-4318) with each altering the interpeptide bridge making it more resistant to cleavage by lysostaphin. Other less well defined mechanisms include those reported for the lyrA gene (lysostaphin resistance A) (Grundling et al. 2006. *J. Bacteriol.* 188: 2463-2472) and SspC (staphostatin B) (Shaw et al. 2005. *J. Bacteriol.* 187: 1751-1762) that when mutated reduced staphylococcal susceptibility to lysostaphin, along with other pleiotropic effects. MRSA have been shown to mutate femA when exposed in vitro or in vivo to sub-inhibitory doses of lysostaphin (Climo et al. 2001. *Antimicrobial Agents and Chemotherapy* 45: 1431-1437.); however, the strains that arise have been reported to show a reduced fitness and are usually susceptible to a second antibiotic (Kusuma et al. 2007. *Antimicrobial Agents and Chemotherapy* 51: 475482).

The finding that a second antimicrobial can alleviate the development of resistant staphylococcal strains is a strong argument for the use of dual agents in treating MRSA infections. Synergy with lysostaphin has been reported previously (see introduction). We demonstrate synergy in the checkerboard assay between lysostaphin and LysK on the MRSA strain USA300 and the mastitis causing strain *S. aureus* 305. Three effective conditions were identified in FIG. 5, with lysostaphin and LysK clearing microtiter wells at concentrations that were less than 30%, 18% and 16%, 33%, respectively of each agents' MIC. The $\Sigma$FIC was 0.449+/−0.069 suggesting strong synergistic activity (Hall et al. 1983. *J. Antimicrob. Chemother.* 11: 427-433). Synergy reduces the amount of agent required to achieve the same effect and this can be very helpful in avoiding adverse effects such as toxicity, immunogenic host response, and putative resistance development.

The mechanism behind the synergy we observe is unknown. Others have proposed that with each enzyme cleaving a different peptidoglycan bond, the two enzymes aid each other in gaining access to (up to 40 layers of) the peptidoglycan (Djurkovic et al., supra; Fischetti, supra; Loeffler et al., supra). However, the simultaneous use of two peptidoglycan hydrolase enzymes is not required for antimicrobial synergy. Lysostaphin is known to also be synergistic with β-lactam antibiotics (Kiri et al., supra) or the ranalexin peptide (Graham and Coote, supra). Similarly, lysozyme and mammalian cationic peptides show synergy against multiple gram negative bacteria, but not with any MRSA tested (Yan and Hancock. 2001. *Antimicrobial Agents and Chemotherapy* 45:1558-1560). The streptococcal phage lytic enzyme Cpl-1 was synergistic with gentamycin and penicillin against several penicillin-resistant and -sensitive *S. pneumonia* strains (Djurkovic et at., supra; Loeffler and Fischetti, supra).

A potentially increased antimicrobial value might be achieved in the use of LysK through the fact that LysK has two lytic domains (CHAP endopeptidase and amidase) and here, the determination of different cut sites, as described below, aids in achieving synergy. Thus far, only peptidoglycan hydrolases (e.g. bacteriophage endolysins, lysostaphin) harboring single lytic domains have been tested for synergy in vitro or in animal models (reviewed in the introduction).

According to the present invention, the terms "nucleic acid molecule", "nucleic acid sequence", "polynucleotide", "polynucleotide sequence", "nucleic acid fragment", "isolated nucleic acid fragment" are used interchangeably herein. These terms encompass nucleotide sequences and the like. A polynucleotide may be a polymer of RNA or DNA that is single-or double-stranded and that optionally contains synthetic, non-natural or altered nucleotide bases. A polynucleotide in the form of a polymer of DNA may be comprised of one or more segments of cDNA, genomic DNA, synthetic DNA, or mixtures thereof. This will also include a DNA sequence for which the codons encoding the LysK prophage endolysin according to the invention will have been optimized according to the host organism in which it will be expressed, these optimization methods being well known to those skilled in the art.

The term "isolated" polynucleotide refers to a polynucleotide that is substantially free from other nucleic acid sequences, such as other chromosomal and extrachromosomal DNA and RNA, that normally accompany or interact with it as found in its naturally occurring environment. However, isolated polynucleotides may contain polynucleotide sequences which may have originally existed as extrachromosomal DNA but exist as a nucleotide insertion within the isolated polynucleotide. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "construct" refers to a recombinant nucleic acid, generally recombinant DNA, that has been generated for the purpose of the expression of a specific nucleotide sequence(s), or is to be used in the construction of other recombinant nucleotide sequences. A "construct" or "chimeric gene construct" refers to a nucleic acid sequence encoding a protein, operably linked to a promoter and/or other regulatory sequences.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter) or a DNA sequence and a regulatory sequence(s) are connected in such a way as to permit gene expression when the appropriate molecules (e.g., transcriptional activator proteins) are bound to the regulatory sequence(s).

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter.

The term "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. "cDNA" refers to a DNA that is complementary to and derived from an mRNA template.

As used herein, "recombinant" refers to a nucleic acid molecule which has been obtained by manipulation of genetic material using restriction enzymes, ligases, and similar genetic engineering techniques as described by, for example, Sambrook et at 1989. *Molecular Cloning: A Laboratory Manual*, Second Edition, Cold Spring Harbor Laboratory Press, Cold Spring Harbor, N.Y. or DNA Cloning: A Practical Approach, Vol. I and II (Ed. D. N. Glover), IRL Press, Oxford, 1985. "Recombinant," as used herein, does not refer to naturally occurring genetic recombinations.

As used herein, the terms "encoding", "coding", or "encoded" when used in the context of a specified nucleic acid mean that the nucleic acid comprises the requisite information to guide translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in CDNA).

A "protein" or "polypeptide" is a chain of amino acids arranged in a specific order determined by the coding sequence in a polynucleotide encoding the polypeptide. Each protein or polypeptide has a unique function.

The invention includes functional LysK prophage endolysin polypeptide and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of LysK prophage endolysin" refers to all fragments of LysK prophage endolysin that retain LysK prophage endolysin activity and function to lyse staphylococcal bacteria.

Modifications of the LysK prophage endolysin primary amino acid sequence may result in further mutant or variant proteins having substantially equivalent activity to the LysK prophage endolysin polypeptides described herein. Such modifications may be deliberate, as by site-directed mutagenesis, or may occur by spontaneous changes in amino acid sequences where these changes produce modified polypeptides having substantially equivalent activity to the LysK prophage endolysin polypeptide. Any polypeptides produced by minor modifications of the LysK prophage endolysin primary amino acid sequence are included herein as long as the biological activity of LysK prophage endolysin is present; e.g., having a role in pathways leading to lysis of staphylococcal bacteria.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. An indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Thus, isolated sequences that encode a LysK prophage endolysin polypeptide and which hybridize under stringent conditions to the LysK prophage endolysin sequences disclosed herein, or to fragments thereof, are encompassed by the present invention.

Substantially similar nucleic acid fragments of the instant invention may also be characterized by the percent identity of the amino acid sequences that they encode to the amino acid sequences disclosed herein, as determined by algorithms commonly employed by those skilled in this art. Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol Biol.* 48:443).

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise a particular plant protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as Well as substantial portions at those sequences as defined above.

Fragments and variants of the disclosed nucleotide sequences and proteins encoded thereby are also encompassed by the present invention. By "fragment" a portion of the nucleotide sequence or a portion of the amino acid sequence and hence protein encoded thereby is intended. Fragments of a nucleotide sequence may encode protein fragments that retain the biological activity of the native protein and hence have LysK prophage endolysin-like activity. Alternatively, fragments of a nucleotide sequence that are useful as hybridization probes may not encode fragment proteins retaining biological activity.

By "variants" substantially similar sequences are intended. For nucleotide sequences, conservative variants include those sequences that, because of the degeneracy of the genetic code, encode the amino acid sequence of one of the LysK prophage endolysin polypeptides of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, LysK prophage endolysin activity as described herein. Such variants may result from, for example, genetic polymorphism or from human manipulation. Biologically active variants of a native LysK prophage endolysin protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired LysK prophage endolysin activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of LysK prophage endolysin protein can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

The staphylococcal control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with milk or milk by-products or human and veterinary applications. Likewise, ingredients may be selected for any given composition which are cooperative in their combined effects whether incorporated for antimicrobial efficacy, physical integrity of the formulation or to facilitate healing and health in medical and veterinary applications, including for example in the case of mastitis, healing and health of the teat or other human or animal body part. Generally, the composition comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these, or attached to a solid stratum such as colloidal gold. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms involved, should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Plasmids, Constructs and Strains

All subcloning was performed in *E. coli* DH5α (Invitrogen, Carlsbad, Calif.) for plasmid DNA isolation and sequence verification of all constructs. pET21a constructs were induced in *E. coli* BL21 (DE3) (EMD Biosciences, San Diego, Calif.). *Staphylococcus aureus* Newbolt 305 capsular polysaccharide serotype 5 (ATCC 29740) and the MRSA strain USA300 (NARSA NRS384) were grown at 37° C. in Brain Heart Infusion broth (BD, Sparks, Md.) or Tryptic Soy Broth (BD, Sparks, Md.).

The LysK CDNA was kindly provided by Paul Ross (O'Flaherty et al., supra). Inducible vector constructs were created in pET21a (EMD Biosciences, San Diego, Calif.) for introduction of a C-terminal His-tag. To simplify the purification of the LysK protein, a recombinant His tag was added to C-terminus of LysK (C-His-LysK) in pET21a.

Lysostaphin is natively expressed by *S. simulans* in the form of an inactive prepropeptide (Williamson et al,. 1994. *Appl. Environ. Microbiol.* 60: 771-776). This version is activated by proteolytic cleavage generating the mature 246 aa lysostaphin molecule. The recombinant lysostaphin protein (Sigma-Aldrich Chem. Co.) used throughout this work contains only the 246 as mature peptide (MW=26.8 kD) consisting of a 154 amino acid LAS metalloprotease domain (Bochtler et at 2004. *Protein Sci.* 13: 854-861) and a 63 amino acid SH3b cell wall binding domain (Pfam domain database: Retrieved from the Internet: <URL: sanger.ac.uk/Software/Pfam/).

LysK is a 495 aa endolysin from *S. aureus* phage K. LysK contains an N-terminal CHAP endopeptidase domain (cysteine, histidine-dependent amido-hydrolases/peptidases), a mid protein Amidase-2 (N-acetyl-muramyl-L-alanine amidase) domain and a C-terminal SH3b cell wall binding domain (Pfam domain database: http:/www.sanger.ac.uk/Software/Pfam/) described previously (O'Flaherty et al. supra).

Figure 1:
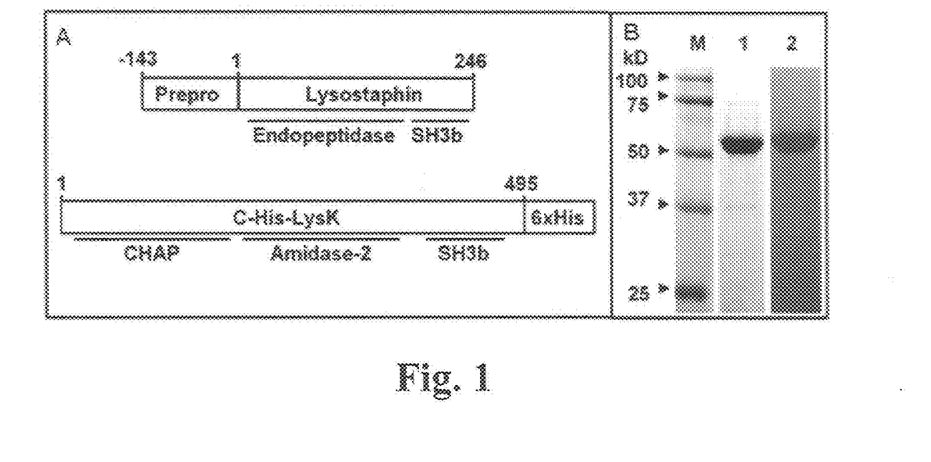
FIGS. 1A and 1B depict the protein organization, purity and zymogram analysis of His-tagged LysK.

The wild type lysostaphin and C-terminal His-tag fusions to the LysK protein are depicted in FIG. 1.

Example 2

PCR Cloning

PCR primers were designed to amplify the wild type LysK gene and introduce appropriate restriction enzyme sites for subcloning into the two vectors. For cloning into pET21a, the LysK sequences were amplified with primers LysK Nde F (5'-GAG AAA TTA CATATG GCT AAG ACT C-3'; SEQ ID NO:1) and LysK Xho R (5'-ATG GTG ATG CTCGAG TTT GAA TAC TCC-3'; SEQ ID NO:2) (engineered restriction enzyme sites are underlined PCR products were gel purified and digested appropriately with enzymes that recognize the engineered sites. The resultant LysK gene fragments were purified over a Micro Bio Spin P30 desalting column (Bio-RAD, Inc.) and introduced into similarly digested, dephosphorylated and gel purified vectors (pET21a) via conventional means. At the C-terminus of the C-tagged LysK, there is an additional 2 amino acids corresponding to the XhoI site (Leu-Glu) followed by 6 His residues.

Example 3

Protein Purification

*E. coli* cultures harboring pET21a derived lysostaphin expression vectors were grown under ampicillin selection to mid log phase ($OD_{600\,nm}$ of 0.4-0.6), chilled on ice for 30 min, induced with 1 mM IPTG(isopropyl-beta-D-thiogalactopyranoside), and incubated at 19° C. with shaking for 18 h. *E. coli* harvested from 100 ml cultures were suspended in 2 ml lysis buffer (50 mM $NaH_2PO_4$, 300 mM NaCl, 10 mM imidazole, pH 8), sonicated on ice for 15×5 sec pulses separated by 15 sec. rests, and centrifuged at 11,000×g for 20 minutes at 4° C. The cleared lysate was transferred to microfuge tubes and centrifuged at 16,000×g for 30 min at 4° C. The cleared supernatant was applied to 1 ml Ni-NTA (nickel matrix) in a slurry and mixed gently for 1 hour at 4° C. (Qiagen). The slurry was loaded into a polypropylene column (Qiagen #34964) where wash and elution buffer profiles were empirically determined for the LysK constructs to be 10 ml of 10 mM imidazole, 20 ml of 20 mM imidazole and elution with 1.2 ml of 250 mM imidazole in the same phosphate buffered saline (50 mM $NaH_2PO_4$, 300 mM NaCl, pH 8.0). Immediately after purification from the nickel column, all samples were brought to 1% glycerol to prevent precipitation of the purified protein. Addition of 1% glycerol has become a routine practice in this lab when isolating His-tagged proteins in order to help resolve solubility issues faced with other His-tagged proteins. All samples were then converted to LysK storage buffer (400 mM NaCl, 20 mM Tris HCl, 1% glycerol, pH 7.5) via Micro Bio Spin P30 desalting column (BioRAD, Inc.) or Zeba desalting column (Pierce) that had been converted to LysK Storage buffer. All samples were then 0.22 micron filter sterilized for use in the MIC assays. After filtration, protein concentration determinations were made via BCA Protein kit (Pierce) and DTT was added to 10 mM after protein concentration determination. Sterilized protein preparations were stored at −80° C. or 4° C. until the time of the assay. Purity of each preparation was determined via SDS-PAGE. Non-tagged lysostaphin was purchased (recombinant, Sigma-Aldrich, L0761). The purified LysK protein and Kaleidoscope protein standards (Invitrogen, Carlsbad, Calif.) were analyzed with 15% SDS-PAGE, with or without 300 ml equivalent of mid log phase *S. aureus* 305 cells ($OD_{600\,nm}$ of 0.4-0.6). Gels were prepared and electrophoresed in Tris-Glycine buffer at 100 volts for 1.5 hours in the BioRad Mini-PROTEAN 3 gel apparatus, according to manufacturers instructions. SDS gels were stained in BioSafe Coomassie stain (BioRad, Hercules, Calif.) for one hour and then rinsed in distilled water overnight. Zymograms were washed in excess water for 1 hour to remove the SDS and incubated at room temperature in water, resulting in areas of clearing in the turbid gel wherever a lytic protein was localized.

A Coomassie stained SDS PAGE of each nickel chromatography purified protein C-His-LysK indicates the quality of the nickel column purification (FIG. 1). A zymogram embedded with mid log phase *S. aureus* 305 cells was run in parallel with the SDS gel (FIG. 1).

Figure 3A:
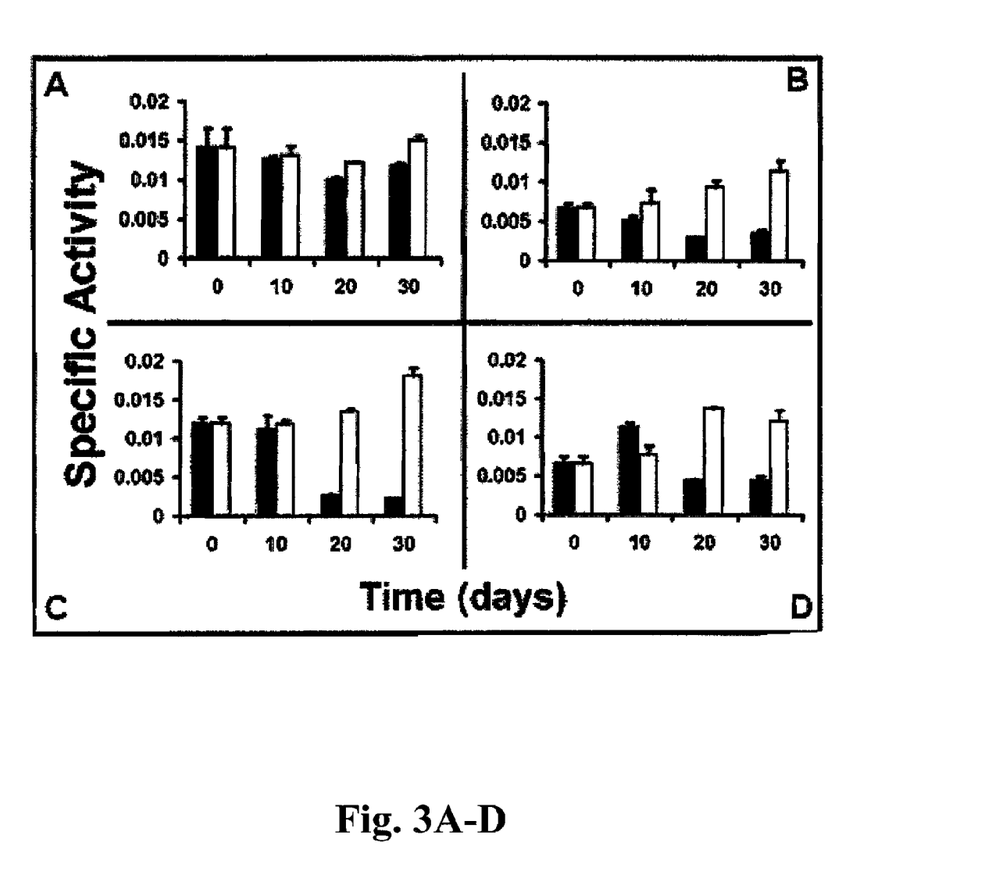

With the goal to use LysK as an antimicrobial, it is important to identify mechanisms for long term storage. Various osmolytes were screened for their ability to increase the stability of stored LysK at −80° C. and 4° C. Purified His-tagged-LysK was stored in any of four buffers and tested weekly. The four buffers were: (a) 400 mM NaCl, 1% glycerol, 10 mM DTT, 20 mM TrisHCl pH 7.5; (b) 400 mM NaCl, 25% glycerol, 10 mM DTT, 20 mM TrisHCl pH 7.5: (c) 2M proline, 1% glycerol, 10 mM DTT, 20 mM TrisHCl pH 7.5 (d) 1M trehalose, 1% glycerol, 10 mM DTT, 20 mM TrisHCl pH 7.5. Fifty microgram aliquots of enzyme in each buffer were stored at −80° C. or 4° C. and removed from storage immediately prior to a turbidity reduction assay where 10 μg were used to examine the effect of storage time and buffer composition on enzyme activity (FIG. 3). As seen in FIG. 3, there is no significant difference between −80° C. treatments (p=higher than 0.05; Anova). However, at 4° C. the 1% glycerol maintains the highest antimicrobial activity against live cells at 30 days (p<0.001; Anova with Tukeys post hoc analysis). Also, there is no significant difference between the 0 day and 30 day 1% glycerol treatment at either 4° C. or −80° C. (p=higher than 0.05; Anova). Due to the advantages afforded by 1% glycerol for maintenance of high activity at either 4° C. or −80° C., all preparations of LysK were subsequently stored in the 1% glycerol buffer immediately after purification. FIG. 3 depicts results of storage LysK. Similar storage activity profiles were obtained with LysK in the optimal storage buffer (400 mM NaCl, 1% glycerol, 20 mM TrisHCl pH 7.5), with similarly high levels of activity maintained for up to 60 days (data not shown).

Example 4

Identification of Peptidoglycan Cleavage Site of the LysK Endopeptidase Domains

The presence of glycopeptides in peptidoglycan digestion mixtures indicates that the peptidoglycan hydrolase possesses both glycosidase and endopeptidase activities. However, peptides in the cell wall digestion mixtures result from cleavages by either two different endopeptidases or an endopeptidase and an N-acetylmuramyl-L-alanine amidase. The structures of these peptides are determined using electrospray ionization mass spectrometric methods, including tandem mass spectrometry (MSMS). Mixtures of peptides were resolved by reverse phase HPLC on a nanobore column connected directly to the mass spectrometer. Knowledge of the peptide structures allows us to deduce the lysin cleavage sites since the structure of the peptidoglycan is known.

Figure 4:
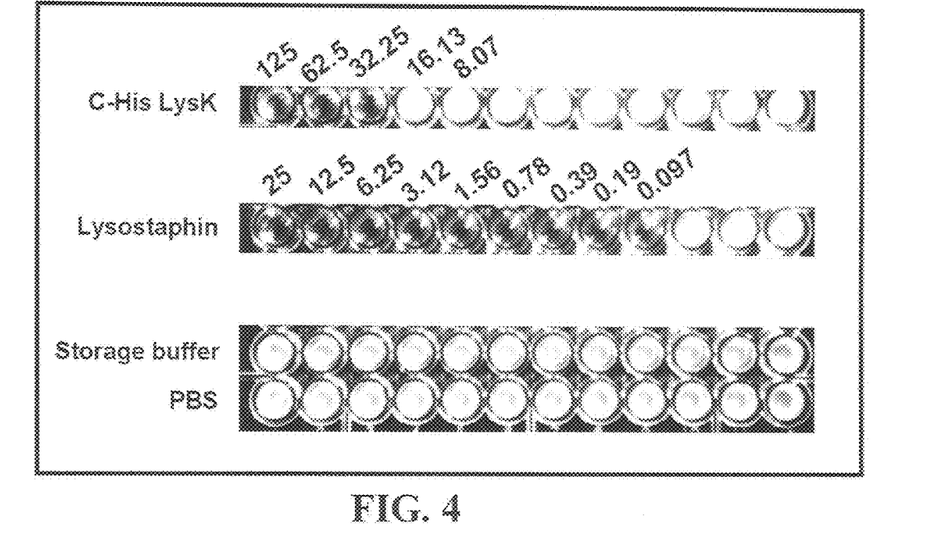
FIG. 4 depicts the peptidoglycan cleavage site of the LysK endopeptidase domains.

Characterization of the peptide products in cell wall digests of LysK resulted in the identification of the two enzymatically active PG lytic domains. One is an amidase that cleaves between N-acetylmuramic acid residues and L-alanine of the stem peptide, and the other is an endopeptidase that cleaves between a D-alanine in the stem peptide and a glycine in the cross-bridge peptide (FIG. 4). Similar activities had previously been reported for the Phi11 lysin. The primary product of LysK digestion was $A_2QKG_5$, which in positive-ion ESI-MS gives a peak with a m/z=702.

Example 5

Turbidity Reduction Assay

The turbidity assay measures the drop in optical density ($OD_{600\,nm}$) resulting from lysis of the target bacteria with the phage endolysin-derived protein. The assay is performed in a Molecular Devices, Spectra Max 340 plate reader. The assay was modified from the cuvette method reported previously (Donovan et al. 2006a. *Appl. Environ. Microbiol* 72: 2988-2996). *S. aureus* is grown to logarithmic phase ($OD_{600\,nm}$=0.4-0.6) at 37° C. in growth media (Typtic Soy Broth, Brain Heart Infusion broth, or Meuller Hinton Broth) with shaking, harvested at 4° C. by centrifugation, and stored on ice until just before the assay when the cells are resuspended to $OD_{600\,nm}$=1.0 in 400 mM NaCl, 20 mM Tris HCl, 1% glycerol, pH 7.5 unless otherwise stated. Enzyme samples are added to three wells of a 96 well dish in 100 μl of buffer. All conditions are performed in triplicate wells. The assay is started by the addition of 100 μl of cells in buffer at $OD_{600nm}$~1.0 via multi channel pipettor. The "no enzyme control" contains buffer and cells, but no enzyme is included. $OD_{600nm}$ readings are taken automatically every 20 seconds. The readings for each well are transferred electronically to an Excel spreadsheet where they are analyzed in a sliding 40 second window over each group of 3 consecutive time points during the five minute period, to identify the highest instantaneous change in $OD_{600nm}$ for each well. The absolute values of $\Delta OD_{600nm}$ for each group of 3 time points is ranked for the entire 5 minute period. A plot of these values vs. time is examined for consistency (bubbles in the well cause high variability) and the highest consistent value is chosen. The highest value representing changes in the $OD_{600nm}$ in the control sample (cells alone) obtained the same way is then subtracted from the highest ranked $\Delta OD_{600nm}$ value for each experimental sample, and the 40 second values for the triplicate samples (wells) are averaged and multiplied by 1.5 to give a $\Delta OD_{600nm}$/minute. This value is then divided by the μg of enzyme protein in the sample to yield a specific activity $\Delta OD_{600nm}$/μg/min. pH Buffers: pH buffers were as follows: 10 mM sodium acetate buffer pH 5, 10 mM sodium acetate buffer pH 6, 10 mM Tris HCl buffer pH 7, 10 mM Tris HCl buffer pH 8, 10 mM Tris HCl buffer pH 9, and 10 mM Carbonate buffer pH 10. Salt Buffers: Salt buffers were composed of 1% glycerol, 20 mM Tris pH 7.5 with varying NaCl from 0-500 mM. Storage Buffers: Storage buffers were composed of 400 mM NaCl, 1% glycerol, 20mm Tris HCl pH 7.5 or with the addition of 1M trehalose, 2M proline, or 25% (final concentration) Glycerol.

Figure 2:
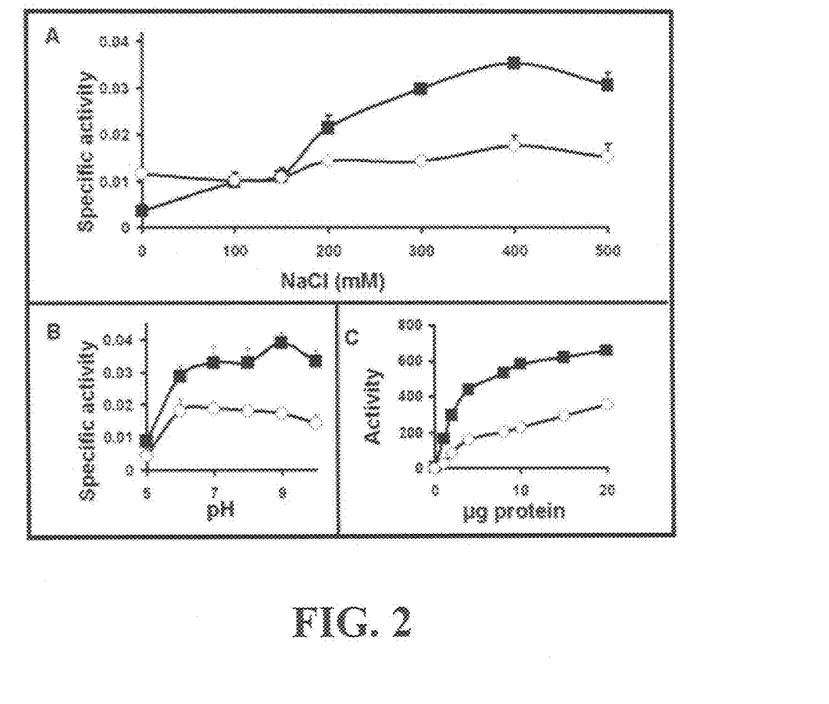
FIG. 2A shows the NaCl optimum of C-His-LysK (10 μg) and lysostaphin (10 μg).
FIG. 2B shows the pH optimum of C-His-LysK (10 μg) and lysostaphin (10 μg) in the turbidity reduction assay.
FIG. 2C depicts the identification of the linear range of protein concentration for C-His-LysK and lysostaphin in the turbidity reduction assay (Error bars are hidden by the enlarged squares and circles). Activity in panel C=Δ $OD_{600\ nm} \times 1000$/min. Specific Activity=Δ $OD_{600\ nm}$/μg/min. Error bars represent SEM for three or more experiments.

To determine the optimal conditions for high antimicrobial activity, LysK and lysostaphin were tested in the turbidity reduction assay with varying salt, pH and protein concentrations against live cells. To determine the optimal salt concentrations for lysostaphin and LysK, S. aureus 305 cells were resuspended in 20 mM Tris pH 7.5 containing 1% glycerol and variable NaCl concentrations ranging from 0-500 mM. The cells were treated with 10 μg of either C-His-LysK or lysostaphin for 5 minutes in the turbidity reduction assay (FIG. 2). Lysostaphin activity is relatively unaffected by salt concentrations between 200 mM to 500 mM whereas LysK shows increasing activity from 150 mM with maximal activity at concentrations approaching 400 mM. LysK has a higher specific activity than lysostaphin at NaCl concentrations greater than 150 mM. To determine the optimal pH, S. aureus 305 cells were resuspended in buffers ranging from pH 5 to pH 10 and treated with C-His-LysK or lysostaphin for 5 minutes (FIG. 2). LysK and lysostaphin show strong activity over a broad pH range from pH 6 to pH 9 similar to previous reports for lysostaphin (Schindler and Schuhardt, supra). The antimicrobial effects of these lysins are near maximal at physiological pH. To determine enzyme concentrations in the turbidity reduction assay that are within the linear range of the assay, S. aureus 305 cells were resuspended in 400 mM NaCl, 1% glycerol, 20 mM Tris pH 7.5 (storage buffer) and treated with varying amounts of C-His-LysK or lysostaphin. Both LysK and lysostaphin demonstrate a linear relationship in the range of 1 to ~5 μg total protein in the assay, under these conditions (FIG. 2).

Example 6

Minimum Inhibitory Concentration

A classical microdilution broth method for determination of the Minimal Inhibitory Concentration (MIC) was used (Jones et al. 1985. In *Manual of Clinical Microbiology*, Balows et al. (Eds.), American Society for Microbiology, Washington D.C., pages 972-977). Briefly, logarithmic-phase bacteria were cultivated in tryptic soy broth and adjusted in broth to a concentration of $1 \times 10^6$ CFU/ml. Sterile microtiter plates containing 100 μl of either LysK or lysostaphin diluted in TSB are inoculated with 100 μl of the bacterial suspension to yield $5 \times 10^5$ CFU/ml. The plate is incubated at 37° C. for 20 h, at which point the plate is analyzed for clear vs. turbid wells. Each MIC assay represents at least two identical determinations per experiment.

Figure 5:
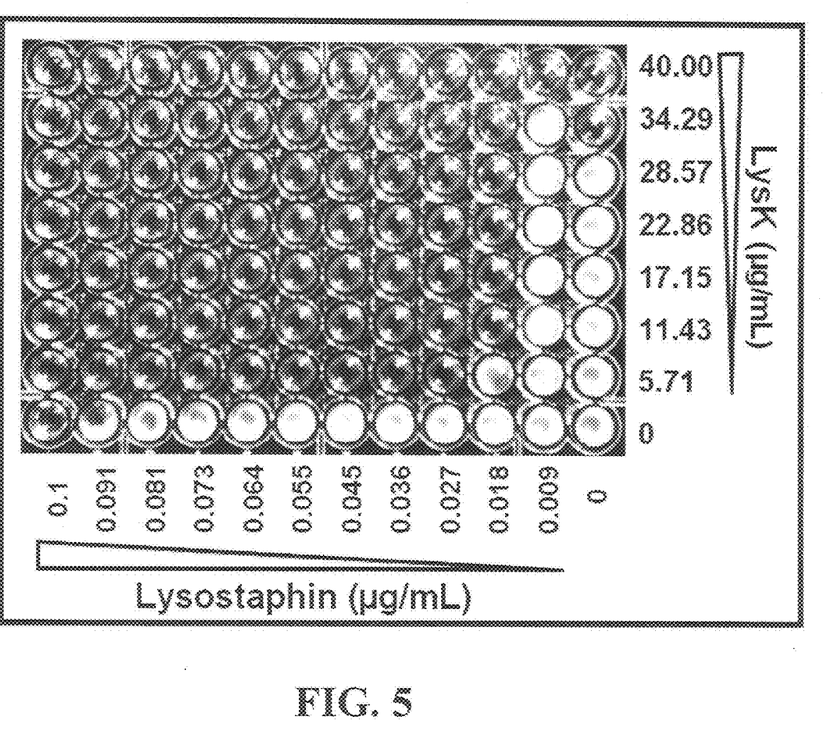
FIG. 5 depicts Minimal Inhibitory Concentration (MIC) determination C-His-LysK and lysostaphin. Values represent µg/ml of each lysin per well. LysK is suspended in storage buffer; lysostaphin is suspended in PBS. Although a representative plate is illustrated, a summary of at least 3 experiments yields an MIC for: Lysostaphin, 0.097 µg/ml+/−0.018; C-His-Lys K, 32.85+/−4.87 µg/ml.

MIC determinations for MRSA strain USA300 by lysostaphin and C-His-LysK, were performed in a 96 well microtiter plate. (FIG. 5). Lysostaphin inhibits growth of MRSA USA 300 at an MIC of 0.096+/−0.018 μg/ml and C-His LysK yields an MIC of 32.85+/−4.87 μg/ml. As expected, neither LysK storage buffer nor PBS had a noticeable effect on the MRSA USA300 cell growth.

Example 7

Synergy

Modified checkerboard assay experiments were performed according to Graham and Coote, supra. S. aureus 305 or MRSA USA300 cells at $1 \times 10^6$ CFU/ml were prepared as for the MIC assay, and added to wells containing varying concentrations of both LysK and lysostaphin diluted in TSB. The amount of buffer in each well was adjusted to maintain the same final concentration of storage buffer (5%) and corrected with 2xTSB to maintain 1xTSB in all wells. The plate was incubated at 37° C. for 20 h, and then analyzed for clear vs. turbid wells. The Fractional Inhibitory Concentration (FIC) is calculated as the MIC of the antimicrobial in combination divided by the MIC of the antimicrobial acting alone. If the sum of the two FICs [ΣFIC=FICA+FICB] is less than 0.5 then there is strong synergy between the two agents (Hall et al., supra).

Figure 6:
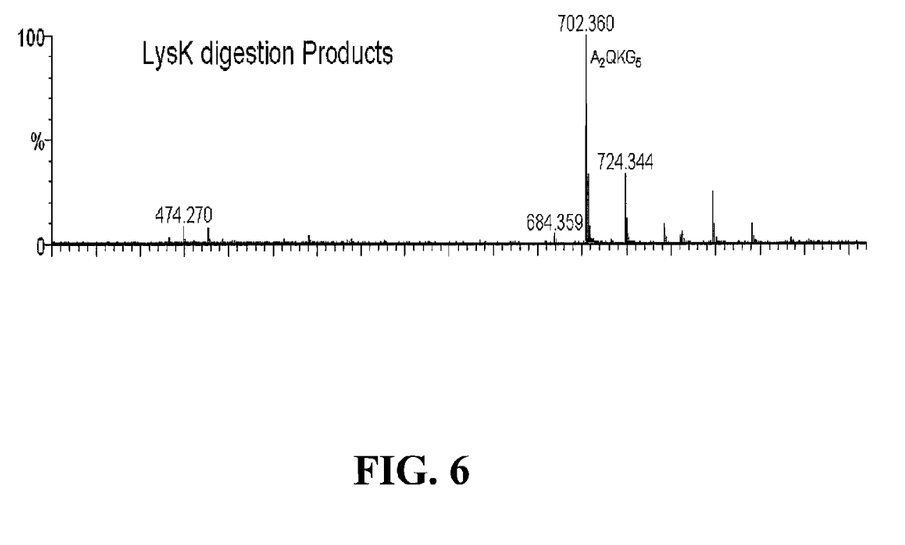
FIG. 6 depicts growth of MRSA USA300 in Tryptic Soy Broth (TSB) after cultivation at 37° C. for 20 hours in 96 well microtiter plates with C-His-LysK, or lysostaphin or combinations of both. LysK and lysostaphin are suspended in LysK storage buffer to maintain a standard composition (5% storage buffer in 1×TSB). The calculated Σ FIC is 0.45+/−0.07, for three experiments indicating strong synergy.

To determine if these proteins could act synergistically, both LysK and lysostaphin were tested in a checkerboard assay with various concentrations of each to determine the minimal concentration of each in combination, that could inhibit growth of the MRSA USA300 (FIG. 6). The last row and column on the 96 well microtiter plate replicate the MIC determinations for lysostaphin and LysK, respectively, with nearly identical results obtained for the MIC in this assay, as in FIG. 5. The pattern of cleared wells demonstrates that the growth inhibition of the two enzymes in combination is greater than either enzyme alone. The two most effective conditions identified in the assay in FIG. 5 were at concentrations of 0.027 and 5.71 μg/ml, and 0.018 and 11.43 μg/ml for lysostaphin and LysK, respectively. These cleared wells corresponded to concentrations that were 30%, 18% and 16%, 33%, respectively of each compounds MIC. It is apparent that the inhibition of growth when the two were added simultaneously was greater than the expected additive effect of each alone. The ΣFIC was 0.45+/−0.07 (three independent experiments), indicating strong synergistic activity (Hall et al., supra), including one assay with S. aureus 305 (data not shown).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An antimicrobial pathogen-specific composition comprising an isolated, recombinant LysK endolysin and an isolated, recombinant lysostaphin and a pharmaceutically acceptable carrier, wherein said composition is functional for degrading the peptidoglycan cell wall of untreated, live *Staphylococcus aureus* including methicillin-resistant *Staphylococcus aureus*.

2. A kit, comprising a composition for treatment of disease caused by the bacteria for which the LysK endolysin and lysostaphin are specific, wherein said kit comprises isolated, recombinant LysK endolysin and isolated, recombinant lysostaphin.

3. The composition of claim 1 wherein the LysK endolysin includes recombinant LysK endolysin comprising an engineered his tag at the C-terminus.

4. A composition useful for the treatment of diseases and infections caused by the bacteria for which the LysK endolysin and lysostaphin are effective against where the composition comprises LysK endolysin and lysostaphin each in amounts that act synergistically together to effectively treat said diseases and infections.

5. A method of treating infection and disease caused by staphylococci in any individual comprising:
   administering to said individual an effective dosage of a composition of any one of claims 3, 4, 1 and 2, wherein said composition comprises an isolated peptidoglycan hydrolase protein having specificity and exolytic activity for the peptidoglycan cell wall of untreated *S. aureus* and wherein said administration is effective for the treatment of *S. aureus* including multi-drug resistant and/or methicillin resistant strains.

6. A method of treating infection and disease caused by methicillin-resistant staphylococci in an individual comprising:
   administering to said individual an effective dosage of a composition of any one of claims 3, 4, 1 and 2, wherein said composition comprises an isolated peptidoglycan hydrolase protein having specificity and exolytic activity for the peptidoglycan cell wall of untreated staphylococci and wherein said administration is effective for the treatment of said methicillin-resistant staphylococci.

7. A method of treating infection and disease caused by methicillin-resistant *S. aureus* (MRSA) in an individual comprising:
   administering to said individual a pathogen-specific antimicrobial composition of any one of claims 3, 4, 1 and 2 comprising an amount of LysK and an amount of lysostaphin each of which alone are ineffective for treating disease and infection caused by MRSA and wherein the composition comprising LysK and lysostaphin in said amounts is synergistically effective having enhanced exolytic activity for the peptidoglycan cell wall of untreated *S. aureus* and said administrating is effective for the treatment of said MRSA.

8. A method of treating mastitis in an animal comprising: administering to said animal an effective dosage of a composition of claims 3, 4, 1 and 2, wherein said composition comprises an isolated or recombinant LysK endolysin and lysostaphin, each having specificity and exolytic activity for the peptidoglycan cell wall of mastitis-causing bacteria wherein said mastitis-causing bacteria are untreated *Staphylococcus aureus* and wherein said administration is effective for reducing the severity of said mastitis.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 1
gagaaattac atatggctaa gactc        25

<210> SEQ ID NO 2
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 2
atggtgatgc tcgagtttga atactcc        27